(12) United States Patent
Robinson et al.

(10) Patent No.: US 9,011,931 B1
(45) Date of Patent: *Apr. 21, 2015

(54) WOUND DRESSING COMPOSITION AND METHOD OF USE

(71) Applicants: Libby Robinson, Memphis, TN (US); Mikel Hays, Hurst, TX (US)

(72) Inventors: Libby Robinson, Memphis, TN (US); Mikel Hays, Hurst, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 14/182,542

(22) Filed: Feb. 18, 2014

Related U.S. Application Data

(63) Continuation-in-part of application No. 13/644,024, filed on Oct. 3, 2012, now Pat. No. 8,828,449.

(60) Provisional application No. 61/590,946, filed on Jan. 26, 2011.

(51) Int. Cl.
| | |
|---|---|
| *A61K 33/00* | (2006.01) |
| *A61K 31/315* | (2006.01) |
| *A61K 31/194* | (2006.01) |
| *A61K 31/28* | (2006.01) |

(52) U.S. Cl.
CPC ............. *A61K 31/315* (2013.01); *A61K 31/194* (2013.01); *A61K 31/28* (2013.01); *Y10S 424/814* (2013.01)

(58) Field of Classification Search
CPC ...... A61K 33/30; A61K 33/10; A61K 33/106
See application file for complete search history.

(56) References Cited

U.S. PATENT DOCUMENTS

| | | |
|---|---|---|
| 5,503,825 A | 4/1996 | Lane |
| 6,228,351 B1 | 5/2001 | Viders |
| 6,479,060 B1 | 11/2002 | Jones et al. |
| 7,223,416 B2 | 5/2007 | Peyman |

OTHER PUBLICATIONS

W. Steven Pray, Treatment of Chapped Lips (Cheilitis), US Pharm. 2005, vol. 5, pp. 68-69 Retrieved from URL:<http://legacy.uspharmacist.com/index.asp?show=article&page=8_1486.htm>.*

* cited by examiner

*Primary Examiner* — Lezah Roberts
*Assistant Examiner* — Nannette Holloman
(74) *Attorney, Agent, or Firm* — Harris, Shelton, Hanover & Walsh; Susan B. Fentress

(57) ABSTRACT

A composition used to facilitate healing of cold sores, fever blisters and canker sore that includes potassium, rubidium, zinc, calcium and sodium is provided. This composition is compounded into a polyethylene glycol ointment containing allantoin (0.5 to 2 percent) and camphor (0.1 to 3 percent) and/or menthol (0.1 to 1 percent). In another embodiment, a method to treat cold sores, fever blisters and canker sores is provided by applying an effective amount of this composition to cold sores, fever blisters and canker sores of a subject in need of treatment thereof.

17 Claims, No Drawings

WOUND DRESSING COMPOSITION AND METHOD OF USE

RELATED PATENT APPLICATIONS

This continuation-in-part application claims the benefit of U.S. provisional patent application Ser. No. 61/590,946, filed on Jan. 26, 2011 under 35 U.S.C. §119(e) and U.S. utility patent application Ser. No. 13/644,024, filed on Oct. 3, 2012, now U.S. Pat. No. 8,828,449 under 35 U.S.C. §111(a); (hereby specifically incorporated herein by reference).

FIELD OF THE INVENTION

This invention relates to a wound dressing composition: particularly, one formulated into a balm to treat cold sores, fever blisters and canker sores in a subject in need of treatment thereof.

BACKGROUND OF THE INVENTION

Normal healing requires a balancing act between the removal of dead tissue and the construction of new tissue. This involves a precise interaction between numerous cell types, as well as growth factors, enzymes and cytokines for normal healing to proceed. The normal healing process should proceed as in the diagram below. Chronic wounds are due to an imbalance in the healing process. Matrix metalloproteinases (MMP) and their inhibitors, (tissue inhibitors of metalloproteinases (TIMPs)) are key for this process to occur in the animals/mammals as well as the human.

In the normally healing wound, various MMPs are expressed throughout the healing process. In chronic wounds, MMP/TIMP imbalances decrease healing. Naturally occurring cations, such as potassium, rubidium, calcium, and zinc, have been shown to regulate protease imbalances, down-regulate the production of reactive oxygen species (ROS) which can damage other molecules and the cell structures of which they are a part, and stimulate re-epithelialization.

U.S. Pat. No. 6,149,947 issued to Hon describes a composition for providing therapeutic efficacy for wound healing containing potassium, rubidium, zinc and calcium ions, in combination with suitable inorganic salts. The Hon synthetic compositions contain by weight of inorganic solids, 10 to 80 parts potassium ions, but preferably 30 to 50 parts potassium ions. This type of product has been applied to open wounds in the skin such as cuts and abrasions in a liquid or spray form.

BRIEF SUMMARY OF THE INVENTION

The present invention relates to a therapeutic composition made of an effective amount of an ingredient including organic salts of naturally occurring cations. These cations have the capacity to facilitate healing of wounds. The naturally occurring cations are ions of potassium, rubidium, zinc, calcium and sodium. In one embodiment, the potassium ranges from 0.60 to 1.60 percent of the composition, sodium ranges from 0.010 to 0.030 percent of the composition, rubidium ranges from 0.003 to 0.030 percent of the composition, calcium ranges from 0.0001 to 0.0003 percent of the composition and zinc ranges from 0.0001 to 0.0005 percent of the composition and the pH ranges from 5 to 7.5. This composition is compounded into a polyethylene glycol ointment containing allantoin (0.5 to 2 percent) and camphor (0.1 to 3 percent) and/or menthol (0.1 to 1 percent).

The preferred weight percent of potassium ranges from 0.60 to 1.60 percent of the composition, sodium ranges from 0.010 to 0.030 percent of the composition, rubidium ranges from 0.003 to 0.030 percent of the composition, calcium ranges from 0.0001 to 0.0003 percent of the composition, and zinc ranges from 0.0001 to 0.0005 percent of the composition. The ingredient, such as naturally occurring cations, are associated with organic anions, such as acetate, hydrogen citrate, di-hydrogen citrate ion, tri-basic citrate ion, and gluconate ion.

In another embodiment, a product made by the process is disclosed. This process involves the steps of: mixing water and organic salts of naturally occurring cations, the cations having the capacity to facilitate healing of wounds, wherein the naturally occurring cations are ions of potassium, rubidium, zinc, calcium and sodium, wherein an amount of potassium ranges from 0.60 to 1.60 weight percent of the product, an amount of sodium ranges from 0.010 to 0.030 weight percent of the product, an amount of rubidium ranges from 0.003 to 0.030 weight percent of the product, an amount of calcium ranges from 0.0001 to 0.0003 weight percent of the product and an admixture amount of zinc ranges from 0.0001 to 0.0005 weight percent of the product, to form an; compounding the admixture with polyethylene glycol to form an ointment; heating the ointment; adding allantoin in the amount of between 0.5 to 2 weight percent of the product to the ointment; adding camphor or menthol to the ointment; reducing the temperature of ointment; and adding a preservative to the ointment to form the product.

In another embodiment, a method to treat cold sores, fever blisters and canker sores is provided by applying an effective amount of this composition to cold sores, fever blisters and canker sores of a subject in need of treatment thereof.

DETAILED DESCRIPTION OF THE INVENTION

The present invention relates to the treatment of cold sores also called "fever blisters." A cold sore is a vesicle that occurs at the junction of the mucous membrane and skin on the lips or nose, and is caused by the virus herpes simplex, type 1. (21 CFR 348.3, Federal Register Vol. 55 No. 21, p. 3382, 31 January, 1990). These blisters are often grouped together in patches. After the blisters break, a crust forms over the resulting sore. Cold sores usually heal within two weeks. Additionally, canker sores can be treated with the present invention. A canker sore is an ulcer in the mouth.

A composition used to facilitate healing of cold sores, fever blisters and canker sores that includes potassium, rubidium, zinc, calcium and sodium is provided. This composition is compounded into a polyethylene glycol ointment containing allantoin (0.5 to 2 percent) and camphor (0.1 to 3 percent) and/or menthol (0.1 to 1 percent). A sufficient amount of an ointment is provided to bulk and carry the organic salts.

The product used to facilitate healing of cold sores, fever blisters and canker sore includes: potassium, rubidium, zinc, calcium and sodium. The preferred weight percent of potassium ranges from 0.60 to 1.60 percent of the composition, sodium ranges from 0.010 to 0.030 percent of the composition, rubidium ranges from 0.003 to 0.030 percent of the composition, calcium ranges from 0.0001 to 0.0003 percent of the composition, and zinc ranges from 0.0001 to 0.0005 percent of the composition. The ingredient, such as naturally occurring cations, is associated with organic anions, such as acetate, hydrogen citrate, di-hydrogen citrate ion, tri-basic citrate ion, and gluconate ion.

This product is combined with ointment-compatible combinations of ingredients permitted by 21 CFR 348.20 (21 CFR 348.3, Federal Register Vol. 55 No. 21, p. 3382, 31 January, 1990) to form a balm. A balm is an ointment or preparation used to heal or soothe the skin. An ointment is a smooth oily preparation that is rubbed on the skin for medicinal purposes or as a cosmetic. The ointment is formed with a polyethylene glycol, such as 400 and 4000. Other ingredients are added to the ointment. These include: allantoin, camphor and menthol. Allantoin is a chemical compound with formula $C_4H_6N_4O_3$. It is also called 5-ureidohydantoin or glyoxyldiureide. It is a di-ureide of glyoxylic acid. Camphor is a waxy, flammable, white or transparent solid with a strong aromatic odor. It is a terpenoid with the chemical formula $C_{10}H_{16}O$. It is found in wood of the camphor laurel (Cinnamomum camphora), a large evergreen tree found in Asia (particularly in Sumatra, Borneo and Taiwan) and also of Dryobalanops aromatica, a giant of the Bornean forests. It also occurs in some other related trees in the laurel family, notably Ocotea usambarensis. Menthol is an optically active organic compound found in peppermint oil and used as an antiseptic, in inhalants, and as an analgesic. Formula: $C_{10}H_{20}O$. A preservative, such as benzoic acid, is added to the ointment as a preservative.

The product is formed by admixing water and all the minerals until they dissolve. As needed, a sufficient amount of KOH is added to adjust the pH within the range 5 to 7.5. In the next step, polyethylene glycol, such as 400 and 4000, is added and the mixture is heated to 150 degrees F. Then allantoin is added and either the camphor or menthol is added to the mixture. After this step, the temperature is decreased to between 120-130 degrees F. and a sufficient amount of benzoic acid is added as a preservative. The product can be formed into a stick or added to a small lidded container and in the finished form can be referred to as a balm.

The balm is applied 2-3 times per day to speed the healing of cold sores/fever blisters and canker sores. The balm can be applied to the lips, skin surrounding the lips and the tissue inside of the mouth and nose.

Formula calculator for cold sore balm is shown in Table 1. In one embodiment an exemplary, balm is prepared with the specific constituents:

TABLE 1

| Component | Amount (grams) |
|---|---|
| Water | 22-30 |
| H$_3$Cit | 0.180 |
| K$_3$Cit•H$_2$O | 1.952 |
| BASE. e.g. KOH (as needed for pH) | — |
| RbC$_2$H$_3$O$_2$ | 0.009 |
| Ca$_3$Cit$_2$•4H$_2$O | 0.001 |
| Zn$_3$Cit$_2$•2H$_2$O | 0.001 |
| Na$_3$Cit•2H$_2$O | 0.075 |
| Benzoic Acid | 0.111 |
| PEG 400 | 31.418 |
| PEG 4000 | 38.253 |
| Allantoin | 0.5-2 |
| Camphor | 0.1-3 |
| Menthol | 0.1-1 |

A study was conducted with twenty subjects to evaluate the use of the composition of invention on the treatment of cold sores, fever blisters and canker sores (intra-oral gingival lesions). The balm of the present invention was applied by the participants 2-3 times per day to determine how rapidly their symptoms and appearance of the lesions would clear up, in their opinion, as compared to their historical experience with ABREVA (SB PHARMCO INC. CORPORATION PUERTO RICO. 30% of the subjects reported the appearance and symptoms (tingling, pain, burning and itching) of their lesions were cleared up in two days. Additionally, 65% reported cold sore/fever blister appearance and symptoms were cleared up within three days. 18 of the 20 subjects stated that pain, itching and burning resolved more quickly with the present composition, and they also reported a 50-60% reduction in healing time as compared to their historical experience with ABREVA (SB PHARMCO INC. CORPORATION PUERTO RICO). Participants reported healing time in as little as one day and the longest took 8 days. Healing is defined as how many days it takes for the cold sore/fever blister to heal as determined by the subject. The present composition reduces inflammation quickly, thereby reducing pain and itching. The symptoms of pain, itching, and burning resolved more quickly with the present composition as compared to the subject's experience with ABREVA (SB PHARMCO INC. CORPORATION PUERTO RICO). The study also provided positive results with respect to canker sores. The ointment was applied inside the mouth 2-3 times per day and healed within three days.

The present composition, as compared to prior art products, such as ABREVA (SB PHARMCO INC. CORPORATION PUERTO RICO), can be applied less frequently while still obtaining beneficial results. ABREVA (SB PHARMCO INC. CORPORATION PUERTO RICO), is required to be applied five times a day, while the present composition only needs to be applied 2-3 times a day. ABREVA (SB PHARMCO INC., PUERTO RICO), does not treat inflammation, while with the present invention reduces inflammation quickly, thereby reducing pain and itching. ABREVA's (SB PHARMCO INC., PUERTO RICO), users reported headaches, redness or swelling, rare allergic reactions, no breast-feeding, precautions with pregnancy, possible drug interaction, harmful if swallowed. ABREVA (SB PHARMCO INC., PUERTO RICO) does not have an indication for use with canker sores.

The lip balm can be in the form of a "chap stick" or can be added to a lidded container for delivery to a subject.

All patents, published patent applications, and other references disclosed herein are hereby expressly incorporated by reference in their entireties.

The functions of several elements may, in alternative embodiments, be carried out by fewer elements, or a single element. Similarly, in some embodiments, any functional element may perform fewer, or different, operations than those described with respect to the illustrated embodiment. While certain embodiments according to the invention have been described, the invention is not limited to just the described embodiments. Various changes and/or modifications can be made to any of the described embodiments without departing from the spirit or scope of the invention. Also, various combinations of elements, steps, features, and/or aspects of the described embodiments are possible and contemplated even if such combinations are not expressly identified herein.

The invention claimed is:

1. A therapeutic composition comprising an effective amount of an ingredient made of organic salts of naturally occurring cations, the cations having the capacity to facilitate healing of wounds, wherein the naturally occurring cations are ions of potassium, rubidium, zinc, calcium and sodium, wherein an amount of potassium ranges from 0.60 to 1.60 weight percent of the composition, an amount of sodium ranges from 0.010 to 0.030 weight percent of the composition, an amount of rubidium ranges from 0.003 to 0.030 weight percent of the composition, an amount of calcium ranges from 0.0001 to 0.0003 weight percent of the composition and an amount of zinc ranges from 0.0001 to 0.0005 weight percent of the composition, a sufficient amount of a base to adjust the pH of the composition within the range of 5 to 7.5; and a sufficient amount of an ointment to provide bulk and carry the organic salts.

2. The composition of claim 1 wherein the ointment comprises polyethylene glycol.

3. The composition of claim 2 wherein the polyethylene glycol is selected from the group consisting of: 400 and 4000.

4. The composition of claim 1 wherein the ointment includes allantoin.

5. The composition of claim 4 wherein the allantoin ranges from 0.5 to 2 weight percent of the composition.

6. The composition of claim 1 wherein the ointment includes camphor.

7. The composition of claim 6 wherein the camphor ranges from 0.1 to 3 weight percent of the composition.

8. The composition of claim 1 wherein the ointment includes menthol.

9. The composition of claim 8 wherein the menthol ranges 0.1 to 1 weight percent of the composition.

10. The composition of claim 1 wherein the base is KOH.

11. The composition of claim 1 further including a sufficient amount of a preservative to preserve the composition.

12. A method to treat cold sores, fever blisters and canker sores comprising the steps of: applying an effective amount of the a therapeutic composition, said composition comprising an effective amount of an ingredient made of an organic salts of naturally occurring cations, the cations having the capacity to facilitate healing of wounds, wherein the naturally occurring cations are ions of potassium, rubidium, zinc, calcium and sodium, and wherein an amount of potassium ranges from 0.60 to 1.60 weight percent of the composition, an amount of sodium ranges from 0.010 to 0.030 weight percent of the composition, an amount of rubidium ranges from 0.003 to 0.030 weight percent of the composition, an amount of calcium ranges from 0.0001 to 0.0003 weight percent of the composition and an amount of zinc ranges from 0.0001 to 0.0005 weight percent of the composition, a sufficient amount of a base to adjust the pH within the range of 5 to 7.5; and a sufficient amount of an ointment to provide bulk and carry the organic salts, wherein the ointment comprises polyethylene glycol and polyethylene glycol, and polyethylene glycol is selected from the group consisting of: 400 and 4000, wherein the ointment includes allantoin and wherein the allantoin ranges from 0.5 to 2 weight percent of the composition, and a sufficient amount of a preservative to preserve the composition; to cold sores, fever blisters and canker sores of a subject in need of treatment thereof.

13. The method of claim 12, wherein the ointment includes camphor and wherein the camphor ranges from 0.1 to 3 weight percent of the composition.

14. The method of claim 12, wherein the ointment includes wherein the ointment includes menthol, and wherein the menthol ranges 0.1 to 1 weight percent of the composition.

15. A product made by the process comprising:
  a. admixing water and an organic salts of naturally occurring cations, the cations having the capacity to facilitate healing of wounds, wherein the naturally occurring cations are ion of: potassium, rubidium, zinc, calcium and sodium, wherein an amount of potassium ranges from 0.60 to 1.60 weight percent of the product, an amount of sodium ranges from 0.010 to 0.030 weight percent of the product, an amount of rubidium ranges from 0.003 to 0.030 weight percent of the product, an amount of calcium ranges from 0.0001 to 0.0003 weight percent of the product and an amount of zinc ranges from 0.0001 to 0.0005 weight percent of the product, to form an admixture;
  b. compounding said admixture with polyethylene glycol to form an ointment;
  c. heating said ointment;
  d. adding allantoin in the amount of between 0.5 to 2 weight percent of said product to said ointment;
  e. adding camphor or menthol to the ointment;
  f reducing the temperature of the ointment; and
  g. adding a preservative to said ointment to form the product.

16. The product of claim 15 wherein camphor comprises between 0.1 to 3 weight percent of the product.

17. The product of claim 15 wherein menthol comprises between 0.1 to 1 percent of the product.

\* \* \* \* \*